United States Patent
Zhou et al.

(10) Patent No.: US 11,492,317 B2
(45) Date of Patent: Nov. 8, 2022

(54) SYNTHESIS OF BIO-BASED POLYOLS FROM EPOXIDIZED CARDANOL AND EPOXIDIZED TRIGLYCERIDE BY USING THIOL-CONTAINING REAGENTS

(71) Applicants: Qixin Zhou, Copley, OH (US); Haoran Wang, Akron, OH (US)

(72) Inventors: Qixin Zhou, Copley, OH (US); Haoran Wang, Akron, OH (US)

(73) Assignee: The University of Akron, Akron, OH (US)

(*) Notice: Subject to any disclaimer, the term of this patent is extended or adjusted under 35 U.S.C. 154(b) by 246 days.

(21) Appl. No.: 16/865,726

(22) Filed: May 4, 2020

(65) Prior Publication Data
US 2020/0347001 A1 Nov. 5, 2020

Related U.S. Application Data

(60) Provisional application No. 62/841,941, filed on May 2, 2019.

(51) Int. Cl.
| | |
|---|---|
| *C07C 39/10* | (2006.01) |
| *C08G 18/32* | (2006.01) |
| *C08G 18/73* | (2006.01) |
| *C07C 37/01* | (2006.01) |
| *C07C 39/08* | (2006.01) |
| *C07C 37/00* | (2006.01) |
| *C07C 29/36* | (2006.01) |

(52) U.S. Cl.
CPC ............. *C07C 39/10* (2013.01); *C07C 37/004* (2013.01); *C07C 37/01* (2013.01); *C07C 39/08* (2013.01); *C08G 18/3215* (2013.01); *C08G 18/73* (2013.01); *C07C 29/36* (2013.01)

(58) Field of Classification Search
CPC ......... C07C 39/10; C07C 39/08; C07C 37/01; C07C 37/004; C07C 29/36
See application file for complete search history.

(56) References Cited

U.S. PATENT DOCUMENTS

| | | | |
|---|---|---|---|
| 2006/0004115 A1 | 1/2006 | Ittara et al. | |
| 2006/0009365 A1* | 1/2006 | Erhan | C10M 135/24 |
| | | | 508/491 |
| 2010/0190951 A1 | 7/2010 | Suppes et al. | |
| 2012/0064322 A1* | 3/2012 | Upshaw | C08L 61/20 |
| | | | 428/537.1 |

OTHER PUBLICATIONS

"Synthesis of Hydroxy Thio-ether Derivatives of Vegetable Oil", J. Agric. Food Chem. 2006, 54, 9866-9872, to Sharma et al.*
Suresh et al.; Synthesis, Structure, and Properties of Novel Polyols from Cardanol and Developed Polyurethanes; Ind. Eng. Chem. Res. 2005, 44, 4504-4512; India.

(Continued)

*Primary Examiner* — Michael L Leonard
(74) *Attorney, Agent, or Firm* — Renner Kenner Greive Bobak Taylor & Weber

(57) ABSTRACT

The present invention relates to a bio-based polyol comprising a thiol-epoxy reaction product of an epoxidized nut or seed oil derivative, and a thiol-containing reactant. The bio-based polyol of the present invention can then be combined with a diisocyanate or a polymeric isocyanate to create a polyurethane material.

5 Claims, 2 Drawing Sheets

(56) References Cited

OTHER PUBLICATIONS

Zhang et al.; Reduction of Epoxidized Vegetable Oils: A Novel Method to Prepare Bio-Based Polyols for Polyurethanes; Macromol. Rapid Commun. 2014, 35, 1068-1074; United States.
Guo et al.; Structure and Properties of Halogenated and Nonhalogenated Soy-based Polyols; Journal of Polymer Science: Part A: Polymer Chemistry, vol. 38, 3900-3910 (2000); United States.

* cited by examiner

SYNTHESIS OF BIO-BASED POLYOLS FROM EPOXIDIZED CARDANOL AND EPOXIDIZED TRIGLYCERIDE BY USING THIOL-CONTAINING REAGENTS

CROSS-REFERENCE TO RELATED APPLICATIONS

The present application claims the benefit of U.S. Provisional Patent Application No. 62/841,941, filed on May 2, 2019, which is incorporated herein in its entirety.

FIELD OF THE INVENTION

The present invention generally relates to the production of bio-based polyols. More particularly, the present invention relates to the production of bio-based polyols from epoxidized cardanol and epoxidized triglyceride. Most particularly, the present invention relates to the production of bio-based polyols by utilizing a thiol-containing reactant to react with the epoxidized cardanol and epoxidized triglyceride to generate a hydroxyl group.

BACKGROUND OF THE INVENTION

Considering the declining petroleum resources and the environmental problems caused by the petroleum industry, developing bio-based chemicals from renewable sources has received great attention in both academia and industrial professionals. Thermosetting polyurethanes (PUs) are one of the most important polymer materials and have been widely used in fabricating rigid foams, simulated woods, and protective coatings. Polyols and polyisocyanates are the typical components of thermosetting PUs. Currently, most polyurethanes are prepared from petrochemical-based polyether or polyester polyols. Thus, developing bio-based polyols for polyurethane applications is meaningful for sustainability in industry.

Cashew nutshell liquid derived polyols and seed oil derived polyols are of interest because they are produced from renewable and cost-effective feed stock. The main composition of cashew nutshell liquid is cardanol, and seed oils are mainly triglycerides. Cardanol has an unsaturated alkyl phenolic structure which makes it a unique and valuable building block for sustainable materials, such as phenolic resins, epoxy resins, benzoxazine resins, and polyols. Utilization of the reactivity of an epoxide group to synthesize cardanol-based and triglyceride-based polyols has been demonstrated to be an effective strategy. Generally, cardanol or triglyceride is epoxidized first, and then the epoxidized cardanol or epoxidized triglyceride is then utilized to create polyols by different approaches.

For example, U.S. Patent Application No. 2006/004115 to Ittra et al. discloses a process for the preparation of cardanol-based polyol made by oxidation with peroxy acid generated in-situ to give epoxidized cardanol and the epoxide group is then converted to a hydroxyl group in the presence of an organic acid. An article by Kattimuttathu et al. in Industrial & Engineering Chemistry Research from 2005 disclosed a synthesis of cardanol-based polyols from cardanol glycidyl ether by reacting with water and diethanol amine.

U.S. Patent Application No. 2010/0190951 to Suppes et al. discloses a process for preparing soybean oil-based polyols from epoxidized triglyceride by using a hydroxyl-containing reactant. An article by Zhang et al. in Macromolecular Rapid Communications from 2014 discloses a process for the preparation of vegetable-oil-based polyols from epoxidized triglyceride by a reduction reaction. An article by Petrovic et al. in the Journal of Polymer Science: Part A: Polymer Chemistry from 2000 disclosed a method of preparing soybean oil-based polyols from epoxidized triglyceride by using hydrochloric acid, hydrobromic acid, methanol, and hydrogen.

The polyols prepared by the abovementioned methods and processes can then be crosslinked with isocyanates to produce polyurethanes. However, the reported reactions in the above-mentioned works need a high temperature (more than 60° C.) to generate polyols from the epoxidized cardanol or epoxidized triglyceride for an acceptable conversion rate. Thus, there is a need in the art for a more effective process wherein the generation of polyols can be carried out at room temperature.

SUMMARY OF THE INVENTION

A first embodiment of the present invention provides a bio-based polyol comprising a thiol-epoxy reaction product of: an epoxidized nut or seed oil derivative; and a thiol-containing reactant.

A second embodiment of the present invention provides a bio-based polyol as in the first embodiment, wherein the epoxidized nut or seed oil derivative is selected from the group consisting of epoxidized cardanol and epoxidized triglyceride.

A third embodiment of the present invention provides a bio-based polyol as in any of the above embodiments, wherein the thiol-containing reactant has the general formula of SH—R, wherein R is an organic functional group.

A fourth embodiment of the present invention provides a bio-based polyol as in any of the above embodiments, wherein the thiol-containing reactant is selected from the group consisting of 2-mercaptoethan-1-ol, 3-mercaptopropane-1,2-diol, and propane-1-thiol.

A fifth embodiment of the present invention provides a bio-based polyol as in any of the above embodiments, wherein the thiol-epoxy reaction takes place in the presence of a strong base catalyst and a solvent.

A sixth embodiment of the present invention provides a bio-based polyol as in any of the above embodiments, wherein the strong base catalyst is selected from the group consisting of lithium hydroxide (LiOH), sodium hydroxide (NaOH), potassium hydroxide (KOH), 1,8-diazabicyclo[5.4.0]undec-7-ene, and tetrabutylammonium fluoride.

A seventh embodiment of the present invention provides a bio-based polyol as in any of the above embodiments, wherein the solvent is selected from the group consisting of tetrahydrofuran (THF), dimethyl sulfoxide (DMSO), and dimethylformamide (DMF).

An eighth embodiment of the present invention provides a bio-based polyol as in any of the above embodiments, wherein the bio-based polyol has a hydroxyl number between about 200 and about 500 mg/KOH.

A ninth embodiment of the present invention provides a polyurethane comprising the reaction product of: a diisocyanate or a polymeric isocyanate; and a bio-based polyol wherein the bio-based polyol comprises a thiol-epoxy reaction product of: an epoxidized nut or seed oil derivative; and a thiol-containing reactant.

A tenth embodiment of the present invention provides a polyurethane as in the ninth embodiment, wherein the epoxidized nut or seed oil derivative is selected from the group consisting of epoxidized cardanol and epoxidized triglyceride.

An eleventh embodiment of the present invention provides a polyurethane as in either the ninth or tenth embodiments, wherein the thiol-containing reactant has the general formula of SH—R, wherein R is an organic functional group.

A twelfth embodiment of the present invention provides a polyurethane as in any of the ninth through eleventh embodiments, wherein the thiol-containing reactant is selected from the group consisting of 2-mercaptoethan-1-ol, 3-mercaptopropane-1,2-diol, and propane-1-thiol.

A thirteenth embodiment of the present invention provides a polyurethane as in any of the ninth through twelfth embodiments, wherein the thiol-epoxy reaction takes place in the presence of a strong base catalyst and a solvent.

A fourteenth embodiment of the present invention provides a polyurethane as in any of the ninth through thirteenth embodiments, wherein the strong base catalyst is selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride.

A fifteenth embodiment of the present invention provides a polyurethane as in any of the ninth through fourteenth embodiments, wherein the solvent is selected from the group consisting of tetrahydrofuran (THF), dimethyl sulfoxide (DMSO), and dimethylformamide (DMF).

A sixteenth embodiment of the present invention provides a method of preparing a bio-based polyol, the method comprising the steps of: providing an epoxidized nut or seed oil derivative; providing a thiol-containing reactant; and combining the epoxidized nut or seed oil derivative and the thiol-containing reactant so as to create a thiol-epoxy reaction to form the bio-based polyol.

A seventeenth embodiment of the present invention provides a method as in the sixteenth embodiment, wherein the epoxidized nut or seed oil derivative is selected from the group consisting of epoxidized cardanol and epoxidized triglyceride and wherein the thiol-containing reactant has the general formula of SH—R, wherein R is an organic functional group.

An eighteenth embodiment of the present invention provides a method as in either the sixteenth or seventeenth embodiments, wherein the thiol-containing reactant is selected from the group consisting of 2-mercaptoethan-1-ol, 3-mercaptopropane-1,2-diol, and propane-1-thiol.

An nineteenth embodiment of the present invention provides a method as in either the sixteenth or eighteenth embodiments further comprising the steps of: providing a strong base catalyst and a solvent; and combining the strong base catalyst and the solvent with the epoxidized nut or seed oil derivative and the thiol-containing reactant.

A twentieth embodiment of the present invention provides a method as in any of the sixteenth through nineteenth embodiments, wherein the strong base catalyst is selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride and wherein the solvent is selected from the group consisting of tetrahydrofuran (THF), dimethyl sulfoxide (DMSO), and dimethylformamide (DMF).

A twenty-first embodiment of the present invention provides a bio-based polyol comprising a thiol-ene/thiol-epoxy dual reaction product of: an epoxidized nut or seed oil derivative, and a thiol containing reactant, in the presence of light or heat.

A twenty-second embodiment of the present invention provides a bio-based polyol as in the twenty-first embodiment, wherein the epoxidized nut or seed oil derivative is selected from the group consisting of epoxidized cardanol and epoxidized triglyceride.

A twenty-third embodiment of the present invention provides a bio-based polyol as in either of the twenty-first or twenty-second embodiments, wherein the thiol-containing reactant has the general formula of SH—R, wherein R is an organic functional group.

A twenty-fourth embodiment of the present invention provides a bio-based polyol as in any of the twenty-first through twenty-third embodiments, wherein the thiol-containing reactant is selected from the group consisting of 2-mercaptoethan-1-ol, 3-mercaptopropane-1,2-diol, and propane-1-thiol.

A twenty-fifth embodiment of the present invention provides a bio-based polyol as in any of the twenty-first through twenty-fourth embodiments, wherein the thiol-ene/thiol-epoxy dual reaction takes place in the presence of a photoinitiator, a strong base catalyst, and a solvent.

A twenty-sixth embodiment of the present invention provides a bio-based polyol as in any of the twenty-first through twenty-fifth embodiments, wherein the strong base catalyst is selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride.

A twenty-seventh embodiment of the present invention provides a bio-based polyol as in any of the twenty-first through twenty-sixth embodiments, wherein the solvent is selected from the group consisting of tetrahydrofuran (THF), dimethyl sulfoxide (DMSO), and dimethylformamide (DMF).

A twenty-eighth embodiment of the present invention provides a bio-based polyol as in any of the twenty-first through twenty-seventh embodiments, wherein the photoinitiator is selected from the group consisting of 2,2-dimethoxy-2-phenylacetophenone, 2,2-dialkyl-2-hydroxylacetophenones, 2-hydroxy-2-methyl-propiophenone, phenyl bis-(2,4,6-trimethylbenzoyl)-phosphine oxide, benzophenone, and 2-isopropylthioxanthone.

A twenty-ninth embodiment of the present invention provides a bio-based polyol as in any of the twenty-first through twenty-eighth embodiments, wherein the bio-based polyol has a hydroxyl number between about 200 and about 500 mg/KOH.

A thirtieth embodiment of the present invention provides a polyurethane comprising the reaction product of: a diisocyanate or a polymeric isocyanate; and a bio-based polyol wherein the bio-based polyol comprises a thiol-ene/thiol-epoxy dual reaction product of: an epoxidized nut or seed oil derivative, and a thiol-containing reactant in the presence of light or heat.

A thirty-first embodiment of the present invention provides a polyurethane as in the thirtieth embodiment, wherein the epoxidized nut or seed oil derivative is selected from the group consisting of epoxidized cardanol and epoxidized triglyceride.

A thirty-second embodiment of the present invention provides a polyurethane as in either the thirtieth or thirty-first embodiments, wherein the thiol-containing reactant has the general formula of SH—R, wherein R is an organic functional group.

A thirty-third embodiment of the present invention provides a polyurethane as in any of the thirtieth through thirty-second embodiments, wherein the thiol-containing reactant is selected from the group consisting of 2-mercaptoethan-1-ol, 3-mercaptopropane-1,2-diol, and propane-1-thiol.

A thirty-fourth embodiment of the present invention provides a polyurethane as in any of the thirtieth through thirty-third embodiments, wherein the thiol-ene/thiol-epoxy dual reaction takes place in the presence of a photoinitiator, a strong base catalyst, and a solvent.

A thirty-fifth embodiment of the present invention provides a polyurethane as in any of the thirtieth through thirty-fourth embodiments, wherein the strong base catalyst is selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride.

A thirty-sixth embodiment of the present invention provides a polyurethane as in any of the thirtieth through thirty-fifth embodiments, wherein the solvent is selected from the group consisting of tetrahydrofuran (THF), dimethyl sulfoxide (DMSO), and dimethylformamide (DMF).

A thirty-seventh embodiment of the present invention provides a polyurethane as in any of the thirtieth through thirty-sixth embodiments, wherein the photoinitiator is selected from the group consisting of 2,2-dimethoxy-2-phenylacetophenone, 2,2-dialkyl-2-hydroxylacetophenones, 2-hydroxy-2-methyl-propiophenone, phenyl bis-(2,4,6-trimethylbenzoyl)-phosphine oxide, benzophenone, and 2-isopropylthioxanthone.

A thirty-eighth embodiment of the present invention provides a method of preparing a bio-based polyol, the method comprising the steps of: providing an epoxidized nut or seed oil derivative; providing a thiol-containing reactant; and combining the epoxidized nut or seed oil derivative and the thiol-containing reactant in the presence of light or heat so as to create a thiol-ene/thiol-epoxy dual reaction to form the bio-based polyol.

A thirty-ninth embodiment of the present invention provides a method as in the thirty-eighth embodiment, wherein the epoxidized nut or seed oil derivative is selected from the group consisting of epoxidized cardanol and epoxidized triglyceride and wherein the thiol-containing reactant has the general formula of SH—R, wherein R is an organic functional group.

A fortieth embodiment of the present invention provides a method as in either the thirty-eighth or thirty-ninth embodiment, wherein the thiol-containing reactant is selected from the group consisting of 2-mercaptoethan-1-ol, 3-mercaptopropane-1,2-diol, and propane-1-thiol.

A forty-first embodiment of the present invention provides a method as in any of the thirty-eighth through fortieth embodiments, further including the steps of: providing a photoinitiator, a strong base catalyst, and a solvent; and combining the photoinitiator, the strong base catalyst, and the solvent with the epoxidized nut or seed oil derivative and the thiol-containing reactant.

A forty-second embodiment of the present invention provides a method as in any of the thirty-eighth through forty-first embodiments, wherein the photoinitiator is selected from the group consisting of 2,2-dimethoxy-2-phenylacetophenone, 2,2-dialkyl-2-hydroxylacetophenones, 2-hydroxy-2-methyl-propiophenone, phenyl bis-(2,4,6-trimethylbenzoyl)-phosphine oxide, benzophenone, and 2-isopropylthioxanthone.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF ILLUSTRATIVE EMBODIMENTS

Figure 1:
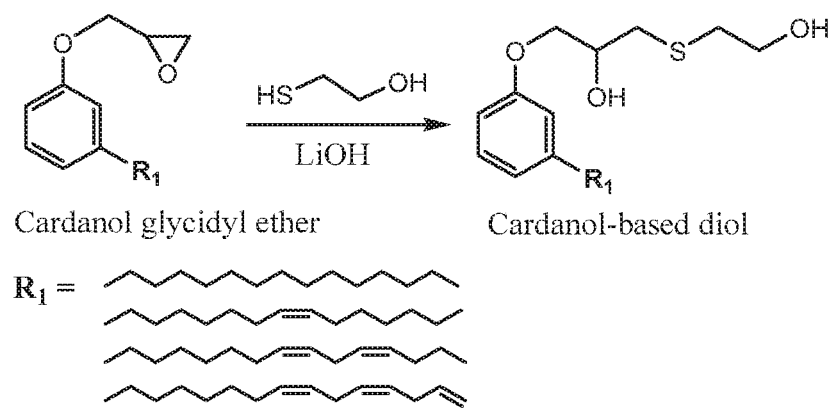
FIG. 1 is a synthetic path for preparing a cardanol-based diol of the present invention.

Embodiments of the present invention are based, at least in part, on a method to prepare bio-based polyols from an epoxidized nut or seed oil derivative such as epoxidized cardanol and epoxidized triglycerides; and a thiol-containing reactant. The method of the present invention can be carried out at room temperature while achieving desirable epoxide group conversion. In the context of the present invention, room temperature is between about 10° C. and about 30° C., in other embodiments between about 15° C. and about 25° C., and in yet other embodiments between about 18° C. and about 22° C. In one or more embodiments of the present invention, the thiol-containing reactant reacts with the epoxide group of the epoxidized nut or seed oil derivative to generate a hydroxyl group. The synthesized bio-based polyols can then be utilized to prepare polyurethanes. The bio-based polyols of the present invention are characterized by a relatively high hydroxyl number. Hydroxyl number is a parameter to describe the content of the hydroxyl group in a given chemical and is based on the titration standard set by ASTM D4274.

In general, the following reagents are added together to create the bio-based polyols of the present invention: a nut or seed oil derivative such as those selected from the group consisting of epoxidized cardanol and epoxidized triglyceride; a thiol-containing reactant wherein the thiol-containing reactant has the general formula of SH—R, wherein R is an organic functional group, and in some embodiments of the present invention, the thiol-containing group is selected from the group consisting of 2-mercaptoethan-1-ol, 3-mercaptopropane-1,2-diol, and propane-1-thiol; a strong base catalyst such as those selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride; and a solvent such as those selected from the group consisting of tetrahydrofuran (THF), dimethyl sulfoxide (DMSO), and dimethylformamide (DMF).

In order to synthesize bio-based polyols with a relatively high hydroxyl number in a more sustainable approach, a thiol-epoxy based click reaction or a thiol-ene/thiol-epoxy dual reaction based click reaction is utilized to synthesize polyol. In general, the thiol-epoxy based click reaction process works as follows: in the presence of the base catalyst, a thiol group from the thiol-containing reactant is first converted to a thiolate anion which is a strong nucleophile. Then, the thiolate anion will attack the less hindered carbon in the epoxidized ring of epoxidized nut or seed oil derivative to form an alkoxide anion. Due to the acidic feature of the thiol molecule and the high basicity of the formed alkoxide anion, homopolymerization of the epoxide group will not happen, and the alkoxide anion will be protonated. Polyols with a relatively high hydroxyl number can be obtained by using the thiol-epoxy reaction between the nut or seed oil derivative and a thiol-containing reactant due to the generation of the additional secondary hydroxyl group.

In one or more embodiments of the present invention, the structure of epoxidized cardanol can be any of the following formulas:

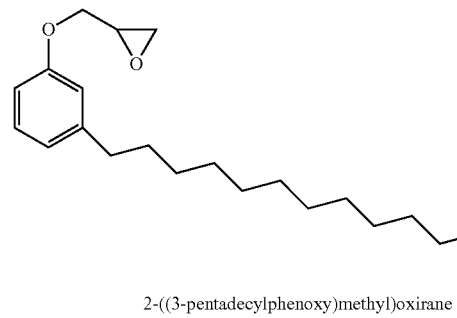

2-((3-pentadecylphenoxy)methyl)oxirane

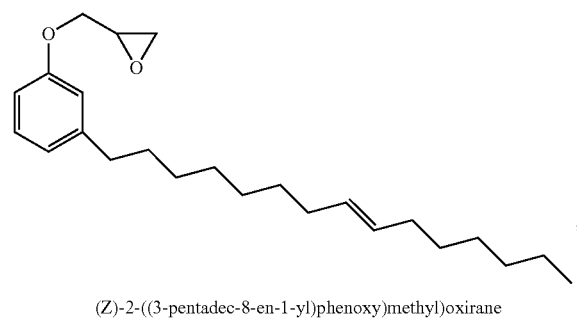

(Z)-2-((3-pentadec-8-en-1-yl)phenoxy)methyl)oxirane

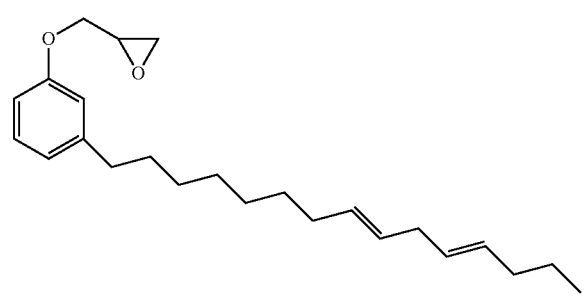 [SMILES: CCC/C=C/C/C=C/CCCCCCCc1cccc(OCC2CO2)c1]

2-((3-((8Z,11Z)-pentadeca-8,11-d;

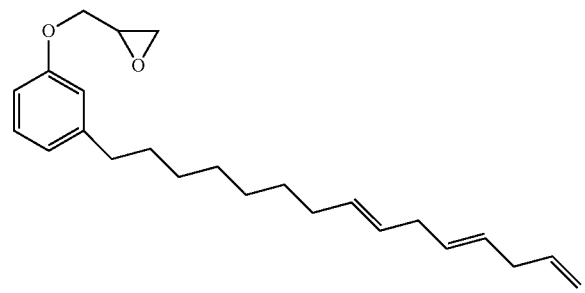 [SMILES: C=CC/C=C/C/C=C/CCCCCCCc1cccc(OCC2CO2)c1]

2-((3-((8Z,11Z)-pentadeca-8,11,14-trien-1-yl)phenoxy)methyl)oxirane;

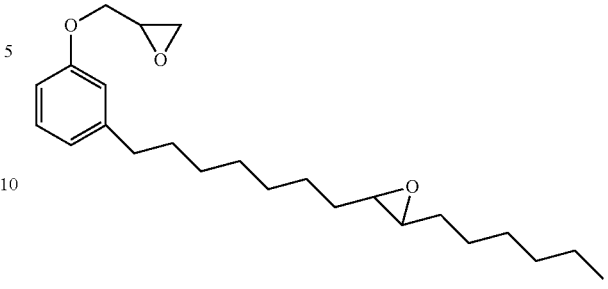

2-hexyl-3-(7-(3-(oxiran-2-ylmethoxy)phenyl)heptyl)oxirane;

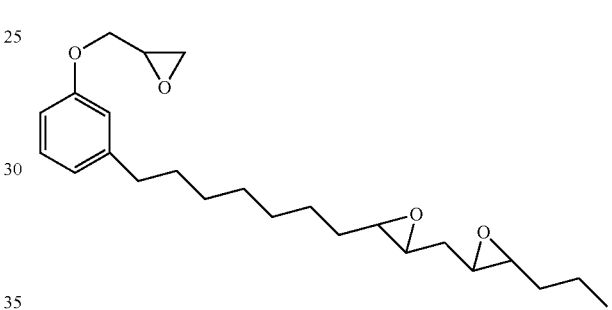

2-(7-(3-(oxiran-2-ylmethoxy)phenyl)heptyl)-3-((3-propyloxiran-2-yl)methyl)oxirane; and

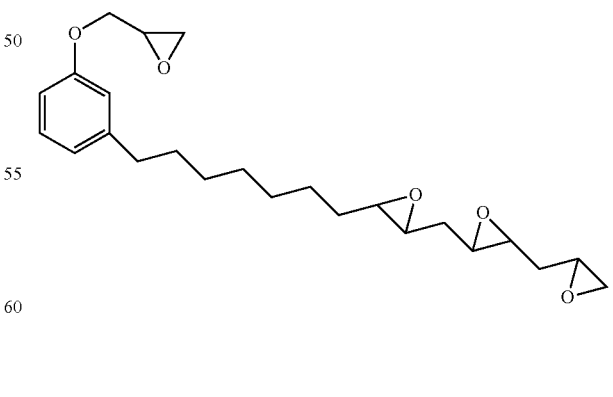

2-(7-(3-(oxiran-2-ylmethoxy)phenyl)heptyl)-3-((3-(oxiran-2-ylmethyl)oxiran-2-yl)methyl)oxirane.

In one or more embodiments of the present invention, the structure of epoxidized triglyceride can be shown as follows:

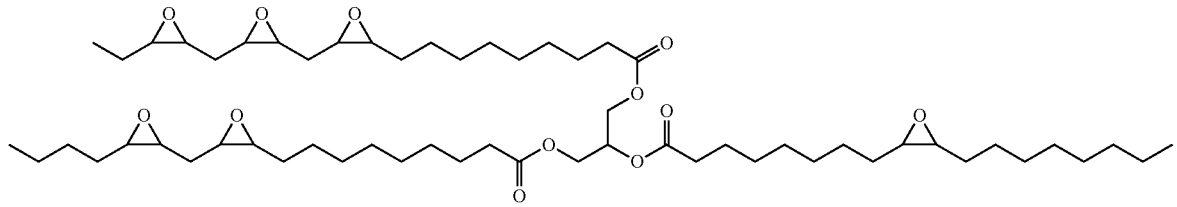 [SMILES: CCCCCCCCC1OC1CCCCCCCC(=O)OC(COC(=O)CCCCCCCCC1OC1CC1OC1CCCC)COC(=O)CCCCCCCCC1OC1CC1OC1CC1OC1CC]

3-((9-(3-((3-butyloxiran-2-yl)methyl)oxiran-2-yl)nonanoyl) oxy)-2-((8-(3-octyloxiran-2-yl)octanoyl)oxy)propyl 9-(3-((3-((3-methyloxiran-2-yl)methyl)oxiran-2-yl)methyl) oxiran-2-yl)nonanoate.

In one or more embodiments, the general synthetic process to create the bio-based polyols of the present invention when utilizing a thiol-epoxy reaction is as follows: adding in the reagents as listed above; then after 4 hours, wash with water; then after extraction takes place, the extracted material is dried and filtered; then after a period of evaporation, the bio-based polyol is produced as the end product. When a thiol-epoxy reaction is utilized to create the bio-based polyols of the present invention, the reaction takes place between the thiol group from the thiol-containing reactant and the epoxy group in the epoxidized cardanol or triglyceride. The step of adding the reagents together takes place by providing an epoxidized nut or seed oil derivative, providing a thiol-containing reactant, and combining the epoxidized nut or seed oil derivative and the thiol-containing reactant so as to create a thiol-epoxy reaction to form the bio-based polyol.

In one or more embodiments, the general synthetic process to create the bio-based polyols of the present invention when utilizing a thiol-ene/thiol-epoxy dual reaction is as follows: adding in the reagents as listed above in addition to a photoinitiator; then after 24 hours, wash with water; then after extraction takes place, the extracted material is dried and filtered; then after a period of evaporation, the bio-based polyol is produced as the end product. When a thiol-ene/thiol-epoxy dual reaction is utilized to create the bio-based polyols of the present invention, the thiol-ene portion of the dual reaction takes place between the thiol group from the thiol-containing reactant and the double bond in the partially epoxidized cardanol or triglyceride which has been initiated by the photoinitiator. The thiol-ene reaction will generate 1 hydroxyl group, while the thiol-epoxy reaction will generate 2 hydroxyl groups. Thus, when a thiol-ene/thiol-epoxy dual reaction is utilized, the hydroxyl number of the polyol produced can be adjusted by utilizing an epoxidized cardanol or triglyceride with different degrees of epoxidation. The step of adding the reagents together takes place by providing an epoxidized nut or seed oil derivative, providing a thiol-containing reactant, and combining the epoxidized nut or seed oil derivative and the thiol-containing reactant in the presence of light or heat so as to create a thiol-ene/thiol-epoxy reaction to form the bio-based polyol.

In one or more embodiments of the present invention, the photoinitiator can be any photoinitiator that will generate radicals. In one or more embodiments, the photoinitiator is selected from the group consisting of 2,2-dimethoxy-2-phenylacetophenone, 2,2-dialkyl-2-hydroxylacetophenones, 2-hydroxy-2-methyl-propiophenone, phenyl bis-(2,4,6-trimethylbenzoyl)-phosphine oxide, benzophenone, and 2-isopropylthioxanthone.

In one or more embodiment, the bio-based polyols of the present invention can be combined with a diisocyanate or a polymeric isocyanate in the presence of suitable catalysts and additives to create polyurethane films. In one or more embodiments of the present invention, the diisocyanate is selected from the group consisting of toluene diisocyanate (TDI), methylene diisocyanate (MDI), hexamethylene diisocyanate (HDI), hydrogenated MDI ($H_{12}$MDI), 4,4'-methylenebis(cyclohexyl isocyanate), and isophorone diisocyanate (IPDI).

In one or more embodiments of the present invention, the bio-based polyol has a hydroxyl number of between about 200 and about 500 mg/KOH, in other embodiments between about 225 and about 475 mg/KOH, and in yet other embodiments between about 250 and about 450 mg/KOH.

Thermogravimetric analysis curves and their derivative curves were taken for PU films of the present invention. The films of the present invention all showed a two-stage degradation process. The first degradation stage is in the range of between about 200 and about 400° C., which is mainly due to the cleavage of the urethane group. The second degradation stage is in the range of between about 400 and about 500° C., which is related to the radical decomposition of the polymer chains. The thermal degradation profiles for the PU films of the present invention vary based on the type of nut or seed oil derivative is used and the amount of phenolic hydroxyl or aliphatic hydroxyl groups are present.

Curves of the storage modulus and loss factor as a function of temperature were also taken for the PU films of the present invention. The temperature at the maximum of the loss factor is defined as the glass transition temperature and from these curves, the cross-link density can also be calculated. PU films of the present invention have a glass transition temperature of between about 40 and about 100° C., in other embodiments between about 45 and about 95° C., and in yet other embodiments between about 50 and about 90° C. PU films of the present invention have a cross-link density of between about 550 and about 1750 mol/m$^3$, in other embodiments between about 600 and about 1650 mol/m$^3$, and in yet other embodiments between about 640 and about 1600 mol/m$^3$. It was found that with increasing hydroxyl number of the polyol used to create the PU films of the present invention, the cross-link density of the PU film is increased. With an increase in the cross-link density, there is an increase in the glass-transition temperature due to the reduction of free volume. In addition, only one peak was found for the PU films of the present invention in the curve of the loss factor, which indicates the homogeneous performance of the PU films of the present invention.

Stress-strain curves were also made for the PU films of the present invention. The elastic modulus, tensile strength, elongation at break, hardness, and reverse impact resistance were determined. PU films of the present invention have an elastic modulus between about 300 and about 1200 MPa, in other embodiments between about 400 and about 1100 MPa, and in yet other embodiments between about 450 and about 1000 MPa. PU films of the present invention have a tensile strength between about 18 and about 55 MPa, in other embodiments between about 20 and about 50 MPa, and in yet other embodiments between about 23 and about 48 MPa. PU films of the present invention have an elongation at break of between about 6 and about 90%, in other embodiments between about 7 and about 88%, and in yet other embodiments between about 8 and about 86%. PU films of the present invention have a Künig pendulum hardness of between about 100 and about 200 seconds, in other embodiments between about 110 and about 190 seconds, and in yet other embodiments between about 115 and about 185 seconds. PU films of the present invention have a pencil hardness of between about H and about 4H. PU films of the present invention have a reverse impact resistance of between about 30 and about 200 lbs., in other embodiments between about 35 and about 190 lbs., and in yet other embodiments between about 40 and about 180 lbs. Tensile strength has a similar trend as the elastic modulus, while the elongation at break is decreased with increased cross-link density. It has also been found that the PU films of the present invention become harder and more brittle with an increase in cross-link density.

In general, cross-link density plays a critical role in the mechanical properties of thermosetting polymers, as the cross-linking controls the mobility of the polymer chains. The cross-linking density can be controlled by controlling the hydroxyl number of the polyol used to create the PU film, which is in turn controlled by the selection of the nut or seed oil derivative to make the polyol. Beyond that, the control of the cross-link density of the PU film can also be adjusted by controlling the ratio of isocyanate to hydroxyl and the type of isocyanate used during formulation.

In light of the foregoing, it should be appreciated that the present invention significantly advances the art by providing a bio-based polyol that is structurally and functionally improved in a number of ways. While particular embodiments of the invention have been disclosed in detail herein, it should be appreciated that the invention is not limited thereto or thereby in as much as variations on the invention herein will be readily appreciated by those of ordinary skill in the art. The scope of the invention shall be appreciated from the claims that follow.

EXAMPLES

Materials

Cardanol (Ultra LITE 2023) was provided by Cardolite Corporation (NJ, USA). Hexamethylene diisocyanate (HDI) trimer (Desmodur N 3600, NCO equivalent weight=183 grams per equivalent, solvent free) was provided by Bayer Material Science (PA, USA). Anhydrous magnesium sulfate (≥98%), 2,2-dimethoxy-2-phenylacetophenone (99%), 2-mercaptoethanol (≥99%), lithium hydroxide (98%), ethanol (200 proof), dichloromethane (≥99.5%), methyl ethyl ketone (≥99%), dibutyltin dilaurate, dimethyl sulfoxide-$d_6$ (DMSO-$d_6$, 100%), and chloroform-d (CDCl$_3$, 100%) were all provided by Sigma-Aldrich. All chemicals were used without further purification. A pen-ray UV lamp (model 11SC-1L) was purchased from UVP Inc. (CA, USA).

Synthesis of a Cardanol-Based Polyol from Cardanol via Thiol-Ene Reaction

Cardanol (10 g, 0.034 mmol), 2-mercaptoethanol (13.53 g, 0.173 mol), and 2,2-dimethoxy-2-phenylacetophenone (0.07 g, 0.289 mmol) were charged into a Pyrex glass tube equipped with a magnetic stirrer. While stirring at room temperature, the reactants were irradiated by a pen-ray UV lamp (365 nm, 1200 uw/cm$^2$) for 24 hours. After that, the reactants were washed with deionized water three times to remove the excess 2-mercaptoethanol and then extracted by dichloromethane. The dichloromethane phase was dried over anhydrous magnesium sulfate and filtered. Finally, 10.47 grams of a cardanol-based polyol were obtained after removing the dichloromethane by rotary evaporation. The hydroxyl number was 324.35 mg KOH/g, determined by titration according to ASTM D4274 and the hydroxyl equivalent weight was 172.96.

Synthesis of a Cardanol-Based Polyol from Cardanol Glycidyl Ether via Thiol-Ene/Thiol-Epoxy Dual Reactions Cardanol glycidyl ether (10.0 g, 0.028 mol), 2-mercaptoethanol (11.14 g, 0.143 mol), and 2,2-dimethoxy-2-phenylacetophenone (0.06 g, 0.238 mmol) were charged into a Pyrex glass tube equipped with a magnetic stirrer. The cardanol glycidyl ether was synthesized by the reaction of phenolic hydroxyl in cardanol with epichlorohydrin. While being stirred at room temperature, the reactants were irradiated with a pen-ray UV lamp (365 nm, 1200 uw/cm$^2$) for 24 hours. Then a mixture of lithium hydroxide (0.34 g, 0.014 mol) and ethanol (15 g, 0.326 mol) were added to the reactants. The reaction was carried out for 4 hours at room temperature. After the ethanol was removed by rotary evaporation, the crude product was washed with deionized water three times and then extracted with dichloromethane. The dichloromethane phase was dried over anhydrous magnesium sulfate and filtered. Finally, 10.56 g of a cardanol-based polyol was obtained after removing the dichloromethane by rotary evaporation. The hydroxyl number was 357.94 mg KOH/g determined by titration according to ASTM D4274 and the hydroxyl equivalent weight was 156.73.

Synthesis of a Cardanol-Based Polyol from Polyepoxide Cardanol Glycidyl Ether via Thiol-Ene/Thiol-Epoxy Dual Reactions Polyepoxide cardanol glycidyl ether (10.0 g), 2-mercaptoethanol (11.14 g, 0.143 mol), and 2,2-dimethoxy-2-phenylacetophenone (0.02 g, 0.063 mmol) were charged into a Pyrex glass tube equipped with a magnetic stirrer. The polyepoxide cardanol glycidyl ether was synthesized by the epoxidation of the cardanol glycidyl ether.

While being stirred at room temperature, the reactants were irradiated with a pen-ray UV lamp (365 nm, 1200 uw/cm$^2$) for 24 hours. Then a mixture of lithium hydroxide (0.67 g, 0.028 mol) and ethanol (30 g, 0.978 mol) were added to the reactants. The reaction was carried out for 12 hours at room temperature. After the ethanol was removed by rotary evaporation, the crude product was washed with deionized water three times and then extracted with dichloromethane. The dichloromethane phase was dried over anhydrous magnesium sulfate and filtered. Finally, 10.21 g of a cardanol-based polyol was obtained after removing the dichloromethane by rotary evaporation. The hydroxyl number was 440.24 mg KOH/g determined by titration according to ASTM D4274 and the hydroxyl equivalent weight was 127.43.

Synthesis of Cardanol-Based Diols via Thiol-Epoxy Reaction

Cardanol glycidyl ether (10 g, 28 mmol), 2-mercaptoethanol (4.37 g, 56 mmol), LiOH (0.28 g, 14 mmol), and THF (10 g, 0.14 mol) were charged into a round-bottom flask equipped with a magnetic stirrer. After 4 hours, the crude product was washed with deionized water three times and extracted by dichloromethane. The dichloromethane phase was dried over anhydrous magnesium sulfate and filtered. Finally, 9.48 grams of cardanol-based diol was obtained after removing the dichloromethane by rotary evaporation. A Varian Mercury 500 MHz spectrometer was used to take an $^1$H NMR spectra and DMSO-d6 was used as the solvent. The conversion was calculated to be 100% based on the $^1$H NMR integration. The hydroxyl number (mg/KOH) of the synthesized cardanol-based diol was 258.35 which has a hydroxyl equivalent weight of 217.15. The synthetic path for this example is shown in FIG. 1.

Synthesis of Cardanol-Based Polyols via Thiol-Epoxy Reaction

Figure 2:
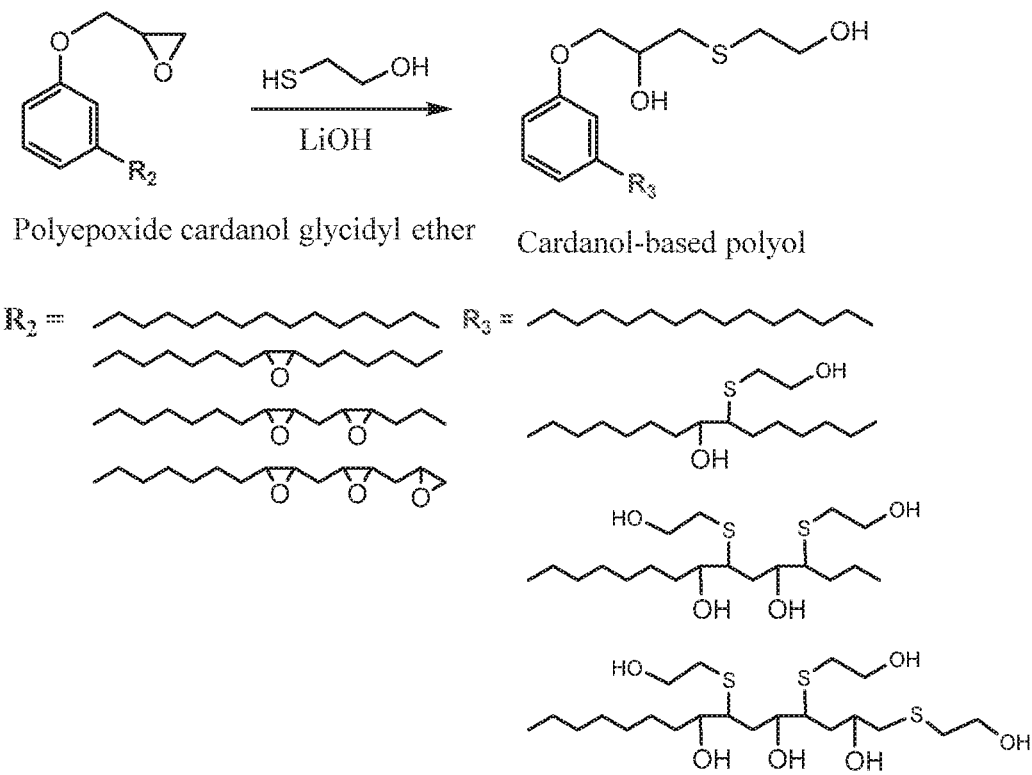
FIG. 2 is a synthetic path for preparing a cardanol-based polyol of the present invention.

Poly epoxide cardanol glycidyl ether (10 g), 2-mercaptoethanol (8.77 g, 0.11 mol), LiOH (0.56 g, 18 mmol) and THF (10 g, 0.14 mol) were charged into a round-bottom flask equipped with a magnetic stirrer. After 4 hours, the crude product was washed with deionized water three times and extracted by dichloromethane. The dichloromethane phase was dried over anhydrous magnesium sulfate and filtered. Finally, 10.13 grams cardanol-based polyol was obtained after removing the dichloromethane by rotary evaporation. A Varian Mercury 500 MHz spectrometer was used to take an $^1$H NMR spectra and DMSO-d6 was used as the solvent. The conversion was calculated to be 100% based on the $^1$H NMR integration. The hydroxyl number (mg/KOH) of the synthesized cardanol-based polyol was 422.92 which has a hydroxyl equivalent weight of 132.65. The synthetic path for this example is shown in FIG. 2.

Synthesis of Triglyceride-Based Polyols via Thiol-Epoxy Reaction

Figure 3:
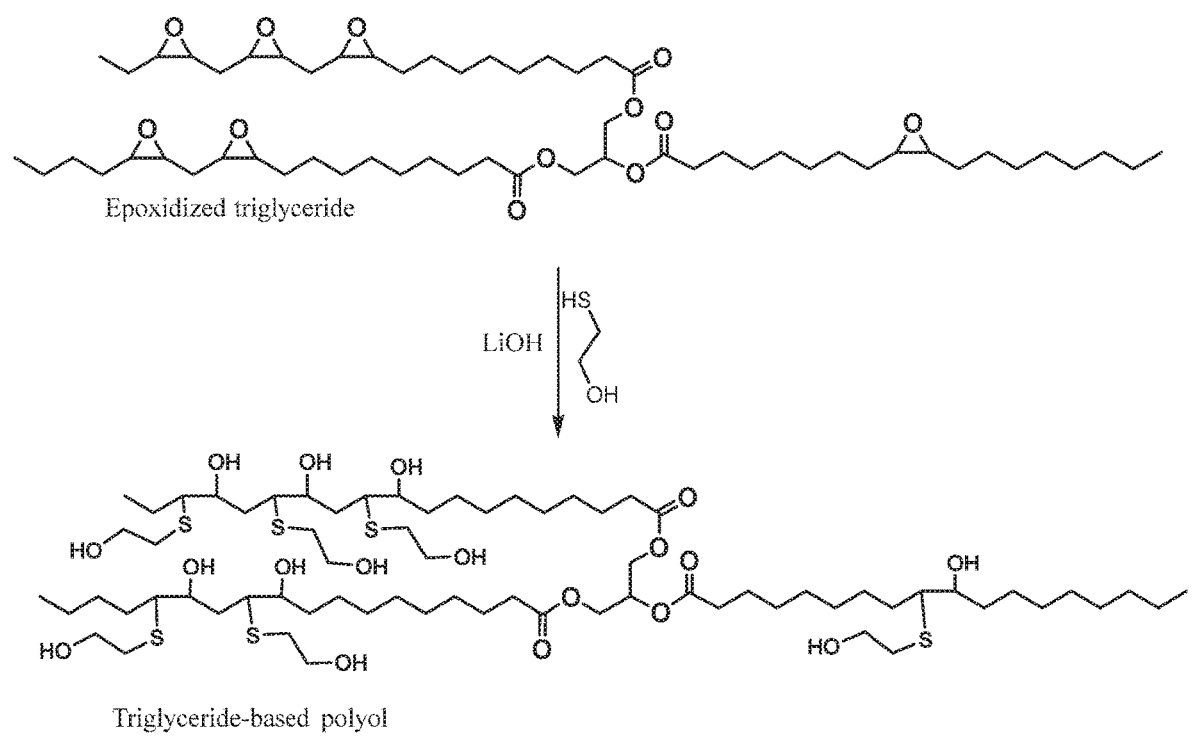
FIG. 3 is a synthetic path for preparing a triglyceride-based polyol of the present invention.

Epoxidized triglyceride (10 g), 2-mercaptoethanol (7.14 g, 91.5 mmol), LiOH (0.46 g, 22.88 mmol), and THF (10 g, 0.14 mol) were charged into a round bottom flask with a magnetic stirrer. After 4 hours, the crude product was washed with deionized water three times and extracted by dichloromethane. The dichloromethane phase was dried over anhydrous magnesium sulfate and filtered. Finally, 10.07 grams triglyceride-based polyol was obtained after removing the dichloromethane by rotary evaporation. A Varian Mercury 500 MHz spectrometer was used to take an $^1$H NMR spectra and DMSO-d6 was used as the solvent. The conversion was calculated to be 100% based on the $^1$H NMR integration. The hydroxyl number (mg/KOH) of the synthesized triglyceride-based polyol was 284.30 which has a hydroxyl equivalent weight of 197.33. The synthetic path for this example is shown in FIG. 3.

Preparation of Thermosetting PU Films

The cardanol-based polyols were combined with an HDI trimer at an NCO/OH ratio of 1.1:1 to prepare the PU films. Methyl ethyl ketone was selected as the solvent, and dibutyltin dilaurate was selected as the curing catalyst. The total formulation of each PU film included 80.0 wt. % polyol and HDI trimer, 19.5 wt. % methyl ethyl ketone, and 0.5 wt. % dibutyltin dilaurate. The films were cast onto cleaned steel panels (QD36, Q-Lab Corporation) and glass panels by a draw-down bar with a wet film thickness of 200 um. The PU films on glass panels were used to make free films. The wet films were kept at room temperature for 6 hours, followed by thermally curing at 100° C. for 1 hour.

What is claimed is:

1. A bio-based polyol comprising a thiol-epoxy reaction product of:
   an epoxidized nut or seed oil derivative; and
   a thiol-containing reactant;
   wherein the thiol-epoxy reaction takes place in the presence of a strong base catalyst and a solvent; wherein the strong base catalyst is selected from the group consisting of lithium hydroxide (LiOH), sodium hydroxide (NaOH), potassium hydroxide (KOH), 1,8-diazobicyclo[5.4.0]undec-7-ene, and tetrabutylammonium fluoride; and wherein the solvent is selected from the group consisting of tetrahydrofuran (THF), dimethyl sulfoxide (DMSO), and dimethylformamide (DMF).

2. The bio-based polyol of claim 1, wherein the epoxidized nut or seed oil derivative is selected from the group consisting of epoxidized cardanol and epoxidized triglyceride; and wherein the thiol-containing reactant has the general formula of SH—R, wherein R is an organic functional group.

3. The bio-based polyol of claim 1, wherein the bio-based polyol has a hydroxyl number between about 200 and about 500 mg/KOH.

4. A method of preparing a bio-based polyol, the method comprising the steps of:
   providing an epoxidized nut or seed oil derivative;
   providing a thiol-containing reactant; and
   combining the epoxidized nut or seed oil derivative and the thiol-containing reactant so as to create a thiol-epoxy reaction to form the bio-based polyol; wherein the thiol-epoxy reaction takes place in the presence of a strong base catalyst and a solvent; wherein the strong base catalyst is selected from the group consisting of lithium hydroxide (LiOH), sodium hydroxide (NaOH), potassium hydroxide (KOH), 1,8-diazobicyclo[5.4.0] undec-7-ene, and tetrabutylammonium fluoride; and wherein the solvent is selected from the group consisting of tetrahydrofuran (THF), dimethyl sulfoxide (DMSO), and dimethylformamide (DMF).

5. The method of claim 4, wherein the epoxidized nut or seed oil derivative is selected from the group consisting of epoxidized cardanol and epoxidized triglyceride and wherein the thiol-containing reactant has the general formula of SH—R, wherein R is an organic functional group.

* * * * *